United States Patent
Herrmann et al.

(10) Patent No.: US 11,826,152 B2
(45) Date of Patent: Nov. 28, 2023

(54) ARRHYTHMIA CLASSIFICATION USING CORRELATION IMAGE

(71) Applicant: Cardiac Pacemakers, Inc., St. Paul, MN (US)

(72) Inventors: Keith L. Herrmann, Minneapolis, MN (US); Krzysztof Z. Siejko, Maple Grove, MN (US); Deepa Mahajan, North Oaks, MN (US); Gezheng Wen, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 336 days.

(21) Appl. No.: 16/886,260

(22) Filed: May 28, 2020

(65) Prior Publication Data

US 2020/0375490 A1     Dec. 3, 2020

Related U.S. Application Data

(60) Provisional application No. 62/853,673, filed on May 28, 2019.

(51) Int. Cl.
| | |
|---|---|
| *A61B 5/363* | (2021.01) |
| *G16H 50/70* | (2018.01) |
| *G16H 10/60* | (2018.01) |
| *G16H 30/20* | (2018.01) |

(Continued)

(52) U.S. Cl.
CPC ............... *A61B 5/363* (2021.01); *A61B 5/35* (2021.01); *A61B 5/352* (2021.01); *G16H 10/60* (2018.01); *G16H 30/20* (2018.01); *G16H 50/70* (2018.01)

(58) Field of Classification Search
CPC .......... A61N 1/363; A61N 1/361; A61N 1/35; A61N 1/339; A61N 1/343; A61B 5/363; A61B 5/361; A61B 5/35; A61B 5/339; A61B 5/343
See application file for complete search history.

(56) References Cited

U.S. PATENT DOCUMENTS

| | | |
|---|---|---|
| 9,451,893 B2 | 9/2016 | Siejko et al. |
| 9,629,565 B2 | 4/2017 | Siejko |
| 10,016,143 B2 | 7/2018 | Siejko |

(Continued)

OTHER PUBLICATIONS

Braunstein, John R., et al., "Autocorrelation of Ventricular Response in Atrial Fibrillation", Circulation Research, vol. IX, Mar. 1961, pp. 300-304.

(Continued)

*Primary Examiner* — George R Evanisko
(74) *Attorney, Agent, or Firm* — Schwegman Lundberg & Woessner, P.A.

(57) ABSTRACT

Systems and methods for classifying a cardiac arrhythmia are discussed. An exemplary system includes a correlator circuit to generate autocorrelation sequences using information of cardiac activity of a subject, including signal segments taken from a cardiac signal at respective elapsed time with respect to reference time. The correlator circuit can generate a correlation image using the autocorrelation sequences. The correlation image may be constructed by stacking the autocorrelation sequences according to the elapsed time of signal segments. An arrhythmia classifier circuit can classify the cardiac activity of the subject as one of arrhythmia types using the correlation image.

20 Claims, 8 Drawing Sheets

(51) Int. Cl.
*A61B 5/35* (2021.01)
*A61B 5/352* (2021.01)

(56) References Cited

U.S. PATENT DOCUMENTS

| | | |
|---|---|---|
| 2005/0004486 A1 | 1/2005 | Glass et al. |
| 2005/0245973 A1* | 11/2005 | Sherman .............. A61N 1/3925 600/518 |
| 2011/0160551 A1 | 6/2011 | Li et al. |

OTHER PUBLICATIONS

Sinal, Mohamad Sabri Bin, et al., "An Efficient Arrhythmia Detection Using Autocorrelation and Statistical Approach", Journal of Computer and Communications, 2018, 6, 63-81.

* cited by examiner

ARRHYTHMIA CLASSIFICATION USING CORRELATION IMAGE

CLAIM OF PRIORITY

This application claims the benefit of priority under 35 U.S.C. § 119(e) of U.S. Provisional Patent Application Ser. No. 62/853,673, filed on May 28, 2019, which is herein incorporated by reference in its entirety.

TECHNICAL FIELD

This document relates generally to medical devices, and more particularly, to systems, devices and methods for detecting and managing cardiac arrhythmias.

BACKGROUND

The heart is the center of a person's circulatory system. The left portions of the heart, including the left atrium (LA) and left ventricle (LV), draw oxygenated blood from the lungs and pump it to the organs of the body to provide the organs with their metabolic needs for oxygen. The right portions of the heart, including the right atrium (RA) and right ventricle (RV), draw deoxygenated blood from the body organs and pump it to the lungs where the blood gets oxygenated. These mechanical pumping functions are accomplished by contractions of the heart. In a normal heart, the sinoatrial (SA) node, the heart's natural pacemaker, generates electrical impulses, called action potentials, that propagate through an electrical conduction system to various regions of the heart to cause the muscular tissues of these regions to depolarize and contract. The electrical conduction system includes, in the order by which the electrical impulses travel in a normal heart, internodal pathways between the SA node and the atrioventricular (AV) node, the AV node, the His bundle, and the Purkinje system including the right bundle branch (which conducts the electrical impulses to the RV) and the left bundle branch (which conducts the electrical impulses to the LV). The electrical impulses travel through an AV conduction pathway to cause the atria, and then the ventricles, to contract.

Tachyarrhythmia occurs when the heart contracts at a rate higher than a normal heart rate. Tachyarrhythmia generally includes supraventricular tachyarrhythmia and ventricular tachyarrhythmia. Ventricular tachyarrhythmia occurs, for example, when a pathological conduction loop formed in the ventricles through which electrical impulses travel circularly within the ventricles, or when a pathologically formed electrical focus generates electrical impulses from the ventricles. Ventricular tachyarrhythmia includes ventricular tachycardia (VT) or ventricular fibrillation (VF). VF is a life threatening condition requiring immediate medical treatment such as ventricular defibrillation. Supraventricular tachyarrhythmia includes physiological sinus tachycardia and pathologic supraventricular tachyarrhythmia. The sinus tachycardia occurs when the sinoatrial (SA) node generates the electrical impulses at a particularly high rate. A pathologic supraventricular tachyarrhythmia occurs, for example, when a pathologic conduction loop forms in an atrium. Supraventricular tachyarrhythmia includes atrial tachyarrhythmia, paroxysmal supraventricular tachycardia, atrioventricular nodal reentrant tachycardia, and atrioventricular reciprocating tachycardia, among others. Atrial tachyarrhythmia includes atrial fibrillation (AF), atrial flutter (AFL), and atrial tachycardia (AT), among others. AF is recognized as the most common clinical arrhythmia. During AF, disorganized electrical pulses originated from regions in or near an atrium may lead to irregular conductions to ventricles, thereby causing inappropriately fast and irregular heart rate. Paroxysmal AF typically lasts from minutes to days before it stops by itself. Persistent AF may last for over a week and typically requires medication or other treatment to revert to normal sinus rhythm. Permanent AF cannot be restored to normal heart rhythm even with treatment. AF may be associated with stroke and requires anticoagulation therapy. AFL usually accompanies with some degree of atrioventricular (AV) node conduction block, and may be associated with a fast and usually regular heart rate. AFL may be associated with a variety of cardiac disorders, such as coronary artery disease (CAD) or hypertensive heart disease. AFL may often degenerate into AF. Prolonged fast AFL may lead to decompensation with loss of normal heart function.

Implantable medical devices (IMDs) have been used to monitor patient health condition or disease states and provide therapies. Some IMDs can detect cardiac arrhythmias, such as atrial tachyarrhythmia or ventricular tachyarrhythmia. For example, implantable cardioverter-defibrillators (ICDs) have been used to monitor patients with abnormal heart rhythms and to deliver electrical energy to the heart to correct the abnormal rhythms. Some IMDs may be used to monitor chronic worsening of cardiac performance, such as due to congestive heart failure (CHF), and to provide cardiac stimulation therapies, including cardiac resynchronization therapy (CRT) to correct cardiac dyssynchrony within a ventricle or between ventricles.

Overview

Embodiments of systems, devices, and methods discussed in this document can improve device-based cardiac arrhythmia detection and classification and provide appropriate and necessary therapies. An exemplary system includes a correlator circuit configured to generate autocorrelation sequences using information of cardiac activity of a subject, such as segments of a cardiac signal with respective elapsed time. The correlator circuit can generate a correlation image, such as by stacking the autocorrelation sequences according to the elapsed time of signal segments. An arrhythmia classifier circuit may be configured to classify the cardiac activity as one of arrhythmia types using the correlation image. The system may initiate or adjust antiarrhythmic therapy according to the classified arrhythmia type.

Example 1 is a medical-device system comprising a correlator circuit and an arrhythmia classifier circuit. The correlation circuit can be configured to receive information of cardiac activity of a subject, to generate autocorrelation sequences using the received cardiac activity information, and to generate a correlation image using a plurality of the generated autocorrelation sequences. The arrhythmia classifier circuit can be configured to classify the cardiac activity of the subject as one of multiple arrhythmia types using the generated correlation image.

In Example 2, the subject matter of Example 1 optionally includes the multiple arrhythmia types that can include an atrial tachyarrhythmia type and a ventricular tachyarrhythmia type.

In Example 3, the subject matter of any one or more of Examples 1-2 optionally includes the information of cardiac activity that can include a cardiac signal, and the correlator circuit can be configured to: generate the autocorrelation sequences using respective signal segments and a plurality of time lags, the signal segments each taken from the cardiac signal and starting at a respective elapsed time after a reference time; and generate the correlation image by stacking a plurality of the generated autocorrelation sequences according to the respective elapsed time of the signal segments.

In Example 4, the subject matter of Example 3 optionally includes the correlator circuit that can be configured to determine a range of heart rates corresponding to the plurality of time lags, and to generate the correlation image including a three-dimensional representation of correlation values over the range of heart rates and a range of elapsed time of the signal segments.

In Example 5, the subject matter of any one or more of Examples 3-4 optionally includes generating an autocorrelation sequence, for a first signal segment taken from the cardiac signal, which can include: selecting a second signal segment from the cardiac signal, the second signal segment including the first signal segment and longer than the first signal segment; generating the autocorrelation sequence, corresponding to the first signal segment, using repeated subtractions of the first signal segment from the second signal segment at a plurality of different time lags.

In Example 6, the subject matter of Example 5 optionally includes the subtractions of the first signal segment from the second signal segment that can be are performed for a plurality of different time lags ranging in time between zero second and a length of the first signal segment.

In Example 7, the subject matter of any one or more of Examples 1-6 optionally includes the arrhythmia classifier circuit that can be configured to extract an image feature from the correlation image, and to classify the cardiac activity of the subject as one of arrhythmia types using the extracted image feature.

In Example 8, the subject matter of Example 7 optionally includes the arrhythmia classifier circuit that can be configured to detect one or more autocorrelation peaks from the correlation image, and to extract the image feature including one or more of an amplitude, a timing, or a scatteredness metric of the detected one or more autocorrelation peaks.

In Example 9, the subject matter of Example 8 optionally includes the arrhythmia classifier circuit that can be configured to detect from the correlation image one or more dominant autocorrelation peaks and one or more non-dominant autocorrelation peaks, and to extract the image feature including a temporal pattern of the one or more dominant autocorrelation peaks and the one or more non-dominant autocorrelation peaks.

In Example 10, the subject matter of any one or more of Examples 1-9 optionally includes the arrhythmia classifier circuit that can be configured to classify the cardiac activity using an image recognition model.

In Example 11, the subject matter of Example 10 optionally includes the image recognition model that can include an arrhythmia template representing a correlation image of a known arrhythmia type, and the arrhythmia classifier circuit can be configured to classify the cardiac activity using a comparison of the generated correlation image to the arrhythmia template.

In Example 12, the subject matter of any one or more of Examples 10-11 optionally includes a controller circuit configured to train the image recognition model using a database of correlation images.

In Example 13, the subject matter of Example 12 optionally includes the controller circuit than can be further configured to update the image recognition model periodically or in response to a user command.

In Example 14, the subject matter of any one or more of Examples 11-13 optionally includes an ambulatory device associated with the subject and a remote computing device configured to communicate with the ambulatory device, the ambulatory device including the arrhythmia classifier circuit, and the remote computing device including the control circuit.

In Example 15, the subject matter of any one or more of Examples 1-14 optionally includes a therapy circuit configured to initiate or adjust a therapy for the subject in response to the classified arrhythmia type.

Example 16 is a method of classifying a cardiac arrhythmia, comprising steps of, via medical-device system: receiving information of cardiac activity of a subject; generating autocorrelation sequences using the received information of cardiac activity via a correlator circuit; generating, via the correlator circuit, a correlation image using the generated autocorrelation sequences; and classifying the cardiac activity of the subject as one of arrhythmia types using the generated correlation image via an arrhythmia classifier circuit.

In Example 17, the information of cardiac activity of Example 16 optionally includes a cardiac signal, and wherein: generating the autocorrelation sequences can include using respective signal segments and a plurality of time lags, the signal segments each taken from the cardiac signal and starting at a respective elapsed time after a reference time; and generating the correlation image can include stacking a plurality of the generated autocorrelation sequences according to the respective elapsed time of the signal segments.

In Example 18, the subject matter of Example 17 optionally includes determining a range of heart rates corresponding to the plurality of time lags, and generating the correlation image including a three-dimensional representation of correlation values over the range of heart rates and a range of elapsed time of the signal segments.

In Example 19, the subject matter of any one or more of Examples 17-18 optionally includes generating an autocorrelation sequence, for a first signal segment taken from the cardiac signal, that can include steps of: selecting a second signal segment from the cardiac signal, the second signal segment including the first signal segment and longer than the first signal segment; and generating the autocorrelation sequence, corresponding to the first signal segment, using repeated subtractions of the first signal segment from the second signal segment at a plurality of different time lags.

In Example 20, the subject matter of any one or more of Examples 16-19 optionally includes extracting an image feature from the correlation image, and classifying the cardiac activity of the subject as one of arrhythmia types using the extracted image feature, wherein the extracted image feature can include one or more of an amplitude, a timing, a scatteredness metric, or a temporal pattern of the detected one or more autocorrelation peaks.

In Example 21, the subject matter of any one or more of Examples 16-20 optionally includes classifying the cardiac activity using an image recognition model.

In Example 22, the subject matter of Example 21 optionally includes training the image recognition model using a database of correlation images.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
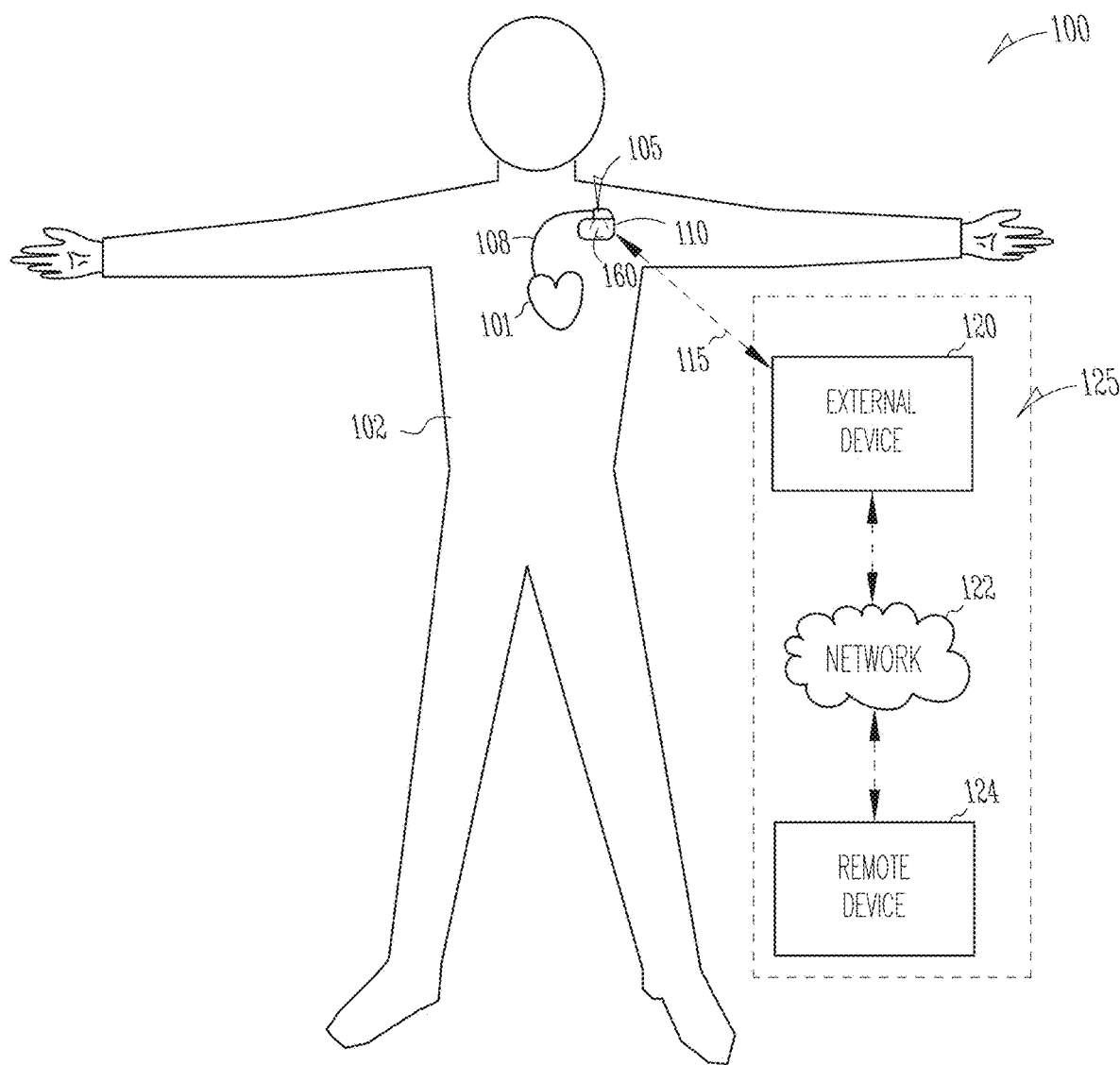
FIG. 1 illustrates generally an example of a patient management system and portions of an environment in which the system may operate.

Ambulatory medical devices (AMD) are used to detect, classify, and treat arrhythmia, including atrial or ventricular tachyarrhythmia. Effective antiarrhythmic treatment requires detecting where the tachyarrhythmia originates. This is sometimes known as arrhythmia classification or arrhythmia discrimination. Examples of the tachyarrhythmia may include sinus tachycardia, AF, AFL, AT, VT, or VF, among others. Arrhythmia classification may be based on heart rates, such as atrial heart rate or ventricular heart rate. For example, atrial heart rate may be compared to ventricular heart rate to determine whether the cardiac activity is atrial tachyarrhythmia or ventricular tachyarrhythmia. Average heart rate and heart rate variability may be used to detect and classify atrial tachyarrhythmia (e.g., AF or AFL). Arrhythmia classification may also be based on cardiac signal morphology. For example, a shape of a cardiac signal (e.g., represented by morphological features) may be compared to a template morphology representing signal shape of a known arrhythmia type, to determine a similarity between the two.

The heart rate-based or morphology-based arrhythmia discrimination may both be affected by the quality of the physiologic signals acquired from the subject. Noises, motion artifacts, or other physiological or non-physiological interferences may introduce over-sensing or under-sensing of atrial or ventricular activations, which lead to inaccurate heart rate estimates, thereby causing false positive or false negative detections of arrhythmia and misclassification of arrhythmia types. Morphological features taken from a cardiac signal may also be prone to noise and interferences. Additionally, signal morphology of a particular arrhythmia type (e.g., VT or AF) may differ from subject to subject, or vary from time to time in the same subject. Consequently, in some cases the morphology may not be robust enough to discriminate different tachyarrhythmia. Misdetection or misclassification of a tachyarrhythmia event may trigger inappropriate therapies, such as a ventricular defibrillation shock delivered to AFL that is misclassified as VT. Inappropriate therapies may be pro-arrhythmic, exacerbate patient cardiac function, and delete device batter power. Misdetection or misclassification may also inappropriately withhold or delay an antiarrhythmic therapy, such as when VT is misclassified as AFL. Inappropriately withholding or delaying an antiarrhythmic therapy may have adverse impact on patient outcome. Furthermore, false alerts to clinicians of the inappropriately detected arrhythmia, or presenting clinicians with a large volume of inappropriately detected arrhythmic events for review or adjudication, may adversely affect the device efficacy and unwarrantedly increase the overall cost of patient management, and diminish the clinical utility of automated device-based arrhythmia detection and discrimination.

For at least the foregoing reasons, the present inventors have recognized a need to improve arrhythmia classification accuracy and robustness, avoid or reduce inappropriate antiarrhythmic therapies (due to misclassification), and improve patient outcome. Disclosed herein are systems and methods for detecting and classifying a cardiac arrhythmia based on a correlation image. An exemplary system includes a correlator circuit configured to generate autocorrelation sequences using information of cardiac activity of a subject, such as segments of a cardiac signal with respective elapsed time. The correlator circuit can generate a correlation image, such as by stacking the autocorrelation sequences according to the elapsed time of signal segments. An arrhythmia classifier circuit may be configured to classify the cardiac activity as one of arrhythmia types using the correlation image. The system may initiate or adjust antiarrhythmic therapy according to the classified arrhythmia type.

The systems, devices, and methods discussed in this document may improve the medical technology of device-based arrhythmia discrimination and treatment. Compared to conventional techniques (e.g., heart rate-based or morphology-based arrhythmia discrimination), the correlation sequences and correlation image discussed in this document are resistant to noise or interferences. The correlation image accentuates signal features such as rhythmicity, variability, autocorrelation peak pattern, etc. that are more discriminative among different arrhythmia types than the features presented in the original cardiac signal. Accordingly, the correlation image-based arrhythmia discrimination discussed herein can improve arrhythmia classification accuracy, and reduce unnecessary or inappropriate therapies as well as inappropriate withholding or delay of appropriate antiarrhythmic therapies.

The correlation image-based arrhythmia discrimination also enhances functionality of an ambulatory medical device. The correlation image-based arrhythmia discrimination improves the sensitivity and specificity of detecting a specified tachyarrhythmia type. In some examples (as discussed further in this document), the correlation image may be constructed using autocorrelation sequences computed using a modified, computationally efficient method based a Minimum Absolute Difference (MAD) function. Compared to conventional correlation computation (which involves a large number of multiplications and additions), the modified autocorrelation method may substantially reduce the computational burden, reduce system complexity and implementation and operation cost. As a result, the correlation image may be constructed in a simpler and less computationally intensive manner, which facilitates its implementation in an ambulatory device, which typically has constraints on power, memory, and computational sources. In some examples, existing system performance may be maintained using lower cost or less obtrusive systems, apparatus, and methods. Moreover, the arrhythmia detection discussed in this document can make more efficient use of device memory by storing information such as correlation image of various types of tachyarrhythmia, which are clinically relevant to treatment and cardiac patient management. With improved arrhythmia detection and classification, fewer alarms are provided, battery life may be extended, fewer unnecessary drugs and procedures may be scheduled, prescribed, or provided, and an overall system cost and power savings may be realized in contrast to existing medical devices and systems.

While the tachyarrhythmia detection and classification system is specifically discussed as part of an AMD (e.g., an implantable device) in this document as an example, the present subject matter applies to tachyarrhythmia classification using a non-implantable system analyzing real-time or previously acquired physiologic information.

FIG. 1 illustrates generally an example of a patient management system 100 and portions of an environment in which the system 100 may operate. The patient management system 100 may perform a range of activities, including remote patient monitoring and diagnosis of a disease condition. Such activities may be performed proximal to a patient, such as in the patient's home or office, through a centralized server, such as in a hospital, clinic or physician's office, or through a remote workstation, such as a secure wireless mobile computing device.

The patient management system 100 may include an ambulatory system 105 associated with a patient 102, an external system 125, and a telemetry link 115 providing for communication between the ambulatory system 105 and the external system 125. The ambulatory system 105 may include an ambulatory medical device (AMD) 110. In an example, the AMD 110 may be an implantable device subcutaneously implanted in a chest, abdomen, or other parts of the patient 102. Examples of the implantable device may include, but are not limited to, pacemakers, pacemaker/defibrillators, cardiac resynchronization therapy (CRT) devices, cardiac remodeling control therapy (RCT) devices, neuromodulators, drug delivery devices, biological therapy devices, diagnostic devices such as cardiac monitors or loop recorders, or patient monitors, among others. The AMD 110 alternatively or additionally may include a subcutaneous medical device such as a subcutaneous monitor or diagnostic device, external monitoring or therapeutic medical devices such as automatic external defibrillators (AEDs) or Holter monitors, or wearable medical devices such as patch-based devices, smart watches, or smart accessories.

By way of example, the AMD 110 may be coupled to a lead system 108. The lead system 108 may include one or more transvenously, subcutaneously, or non-invasively placed leads or catheters. Each lead or catheter may include one or more electrodes. The arrangements and uses of the lead system 108 and the associated electrodes may be determined using the patient need and the capability of the AMD 110. The associated electrodes on the lead system 108 may be positioned at the patient's thorax or abdomen to sense a physiologic signal indicative of cardiac activity, or physiologic responses to diagnostic or therapeutic stimulations to a target tissue. By way of example and not limitation, and as illustrated in FIG. 1, the lead system 108 may be surgically inserted into, or positioned on the surface of, a heart 101. The electrodes on the lead system 108 may be positioned on a portion of a heart 101, such as a right atrium (RA), a right ventricle (RV), a left atrium (LA), or a left ventricle (LV), or any tissue between or near the heart portions. In some examples, the lead system 108 and the associated electrodes may alternatively be positioned on other parts of the body to sense a physiologic signal containing information about patient heart rate or pulse rate. In an example, the ambulatory system 105 may include one or more leadless sensors not being tethered to the AMD 110 via the lead system 108. The leadless ambulatory sensors may be configured to sense a physiologic signal and wirelessly communicate with the AMD 110.

The AMD 110 may be configured as a monitoring and diagnostic device. The AMD 110 may include a hermetically sealed can that houses one or more of a sensing circuit, a control circuit, a communication circuit, and a battery, among other components. The sensing circuit may sense a physiologic signal, such as using a physiologic sensor or the electrodes associated with the lead system 108. Examples of the physiologic signal may include one or more of electrocardiogram, intracardiac electrogram, arrhythmia, heart rate, heart rate variability, intrathoracic impedance, intracardiac impedance, arterial pressure, pulmonary artery pressure, left atrial pressure, right ventricular (RV) pressure, left ventricular (LV) coronary pressure, coronary blood temperature, blood oxygen saturation, one or more heart sounds, intracardiac acceleration, physical activity or exertion level, physiologic response to activity, posture, respiration rate, tidal volume, respiratory sounds, body weight, or body temperature.

The AMD 110 may include a physiologic event detector circuit 160 configured to detect cardiac arrhythmia, and classify the cardiac arrhythmia into one of arrhythmia types such as AF, AFL, AF, SVT, VT, VF, cardiac pauses, among other brady- or tachy-arrhythmia. In some examples, the physiologic event detector circuit 160 may be configured to detect syncope, a presyncopal event or a precipitating event that may lead to a full-blown syncope. In some examples, the physiologic event detector circuit 160 is configured to detect worsening of a chronic medical condition, such as worsening heart failure (WHF). The physiologic event detector circuit 160 may monitor one or more physiologic signals continuously or periodically, and to detect the physiologic event automatically. Additionally or alternatively, the physiologic event detector circuit 160 may be configured to operate in a patient-triggered mode, register a patient-triggered episode and record physiologic data in response to a user-activated trigger. The trigger may be activated by the patient when the patient demonstrates certain signs or symptoms, or experiences a precursor event indicative of a medical event.

The AMD 110 may include a therapy unit that may generate and deliver one or more therapies. The therapy may be delivered to the patient 102 via the lead system 108 and the associated electrodes. The therapies may include electrical, magnetic, or other types of therapy. The therapy may include anti-arrhythmic therapy to treat an arrhythmia or to treat or control one or more complications from arrhythmia, such as syncope, congestive heart failure, or stroke, among others. Examples of the anti-arrhythmic therapy may include pacing, cardioversion, defibrillation, neuromodulation, drug therapies, or biological therapies, among other types of therapies. In an example, the therapies may include cardiac resynchronization therapy (CRT) for rectifying dyssynchrony and improving cardiac function in CHF patients. In some examples, the AMD 110 may include a drug delivery system such as a drug infusion pump to deliver drugs to the patient for managing arrhythmia or complications from arrhythmia.

The external system 125 may include a dedicated hardware/software system such as a programmer, a remote server-based patient management system, or alternatively a system defined predominantly by software running on a standard personal computer or a mobile device. The external system 125 may manage the patient 102 through the AMD 110 connected to the external system 125 via a communication link 115. This may include, for example, programming the AMD 110 to perform one or more of acquiring physiologic data, performing at least one self-diagnostic test (such as for a device operational status), analyzing the physiologic data to detect a cardiac arrhythmia, or optionally delivering or adjusting a therapy to the patient 102. Additionally, the external system 125 may receive device data from the AMD 110 via the communication link 115. Examples of the device data received by the external system 125 may include real-time or stored physiologic data from the patient 102, diagnostic data such as detection of cardiac arrhythmia or events of worsening heart failure, responses to therapies delivered to the patient 102, or device operational status of the AMD 110 (e.g., battery status and lead impedance). The telemetry link 115 may be an inductive telemetry link, a capacitive telemetry link, or a radio-frequency (RF) telemetry link, or wireless telemetry based on, for example, "strong" Bluetooth or WEE 802.11 wireless fidelity "WiFi" interfacing standards. Other configurations and combinations of patient data source interfacing are possible.

By way of example and not limitation, the external system 125 may include an external device 120 in proximity of the AMD 110, and a remote device 124 in a location relatively distant from the AMD 110 in communication with the external device 120 via a telecommunication network 122. Examples of the external device 120 may include a programmer device.

The remote device 124 may be configured to evaluate collected patient data and provide alert notifications, among other possible functions. In an example, the remote device 124 may include a centralized server acting as a central hub for collected patient data storage and analysis. The server may be configured as a uni-, multi- or distributed computing and processing system. The remote device 124 may receive patient data from multiple patients including, for example, the patient 102. The patient data, such as medical event episodes, may be collected by the AMD 110, among other data acquisition sensors or devices associated with the patient 102. The remote device 124 may include a storage unit to store the patient data in a patient database. The storage unit may additionally store an association between a plurality of episode characterizations and a plurality of detection algorithms for detecting a medical event having respective episode characterizations. The server may process the device-generated event episodes to verify that a specific medical event (e.g., a cardiac arrhythmia type) is detected such that the device-detected event is a true positive (TP) detection; or that no such medical event is detected such that the device-detected event is a false positive (FP) detection. The processing of the device-generated medical event episodes may be based on a stored association. In an example, a first event episode may be presented to a user (e.g., a clinician), who would provide an adjudication decision and a first episode characterization. If the adjudication decision indicates that the first event episode is a FP detection, then the server may identify from the stored association a detection algorithm corresponding to the first episode characterization, and process a second event episode using at least the identified detection algorithm to determine that the second event episode is either a TP or a FP detection. The server may schedule a presentation of at least a portion of the second episode using the processing result of the second episode. By using the detection algorithms tailored for recognizing episode with an episode characterization associated with a FP episode, more FP episodes having the same or similar episode characterization may be identified, and therefore avoided from being reviewed and adjudicated by the user. If the second event episode is determined to be a TP episode, then an alert is generated indicating further user review may be warranted.

By way of example, alert notifications may include a Web page update, phone or pager call, E-mail, SMS, text or "Instant" message, as well as a message to the patient and a simultaneous direct notification to emergency services and to the clinician. Other alert notifications are possible. In some examples, the server may include a medical event prioritizer circuit configured to prioritize the alert notifications. For example, an alert of a detected medical event may be prioritized using a similarity metric between the physiologic data associated with the detected medical event to physiologic data associated with the historical alerts.

The remote device 124 may additionally include one or more locally configured clients or remote clients securely connected over the network 122 to the server. Examples of the clients may include personal desktops, notebook computers, mobile devices, or other computing devices. Users, such as clinicians or other qualified medical specialists, may use the clients to securely access stored patient data assembled in the database in the server, and to select and prioritize patients and alerts for health care provisioning. The remote device 124, including the server and the interconnected clients, may execute a follow-up scheme by sending follow-up requests to the AMD 110, or by sending a message or other communication to the patient 102, clinician or authorized third party as a compliance notification.

The network 122 may provide wired or wireless interconnectivity, in an example, the network 122 may be based on the Transmission Control Protocol/Internet Protocol (TCP/IP) network communication specification, although other types or combinations of networking implementations are possible. Similarly, other network topologies and arrangements are possible.

One or more of the external device 120 or the remote device 124 may output the detected medical events to a user such as the patient or a clinician, or to a process including, for example, an instance of a computer program executable in a microprocessor. In an example, the process may include an automated generation of recommendations for a therapy, or a recommendation for further diagnostic test or treatment. In an example, the external device 120 or the remote device 124 may respectively include display units for displaying the physiologic or functional signals, or alerts, alarms, emergency calls, or other forms of warnings to signal the detection of arrhythmia. In some examples, the external system 125 may include an external data processor configured to analyze the physiologic or functional signals received by the AMD 110, and to confirm or reject the detection of the medical events. Computationally intensive algorithms, such as machine-learning algorithms, may be implemented in the external data processor to process the data retrospectively to detect cardia arrhythmia.

Portions of the AMD 110 or the external system 125 may be implemented using hardware, software, firmware, or combinations thereof. Portions of the AMD 110 or the external system 125 may be implemented using an application-specific circuit that may be constructed or configured to perform one or more particular functions, or may be implemented using a general-purpose circuit that may be programmed or otherwise configured to perform one or more functions. Such a general-purpose circuit may include a microprocessor or a portion thereof, a microcontroller or a portion thereof, or a programmable logic circuit, a memory circuit, a network interface, and various components for interconnecting these components. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
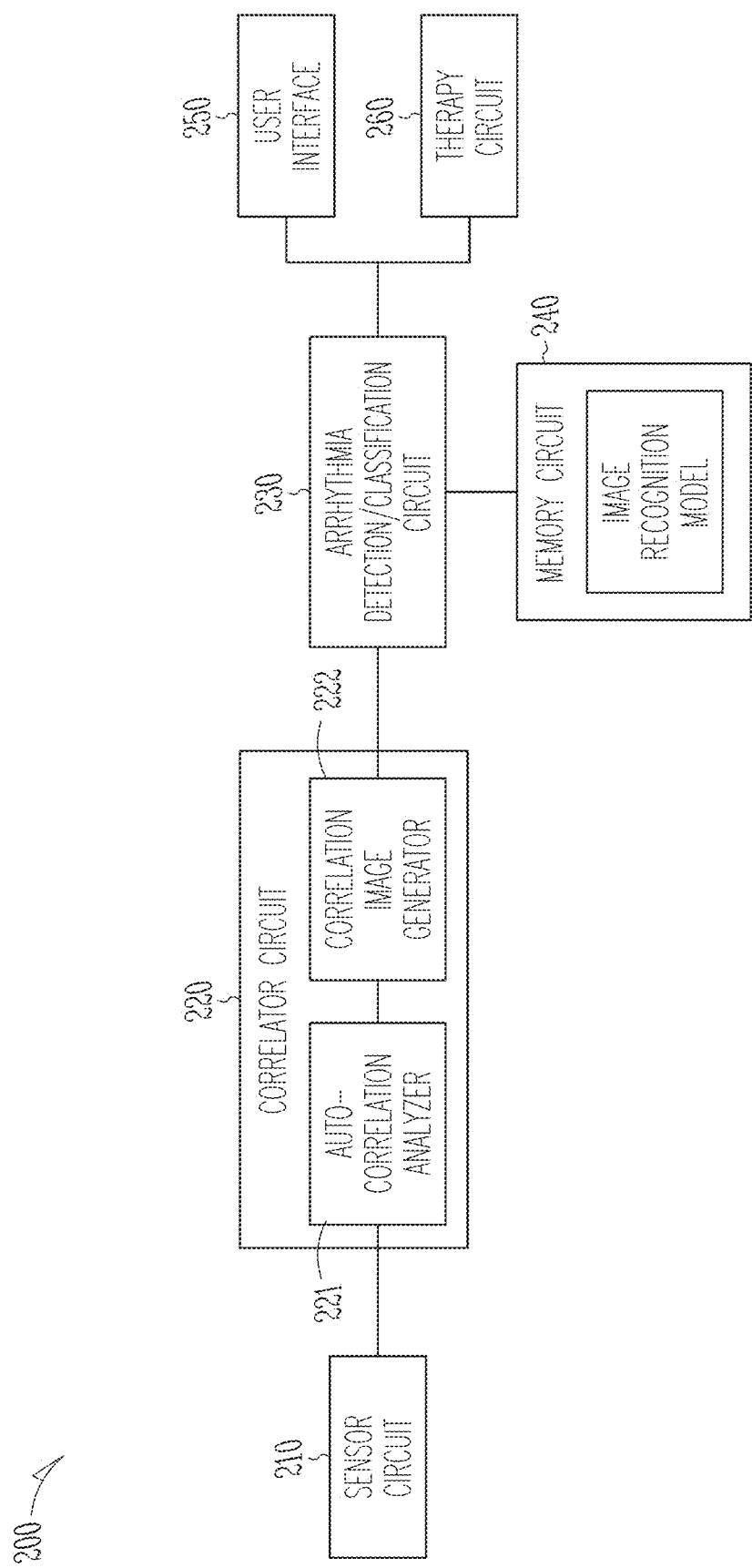
FIG. 2 illustrates generally an example of an arrhythmia detection and classification system configured to detect, and classify the tachyarrhythmia into one of a number of arrhythmia types.

FIG. 2 illustrates generally an example of an arrhythmia detection and classification system 200 configured to detect tachyarrhythmia, and classify the tachyarrhythmia into one of a number of arrhythmia types. Portions of the arrhythmia detection and classification system 200 may be included in the physiologic event detector circuit 160 of the AMD 110. The arrhythmia detection and classification system 200 may include one or more of a sensor circuit 210, a correlator circuit 220, an arrhythmia detection/classification circuit 230, a memory circuit 240, and a user interface unit 250. The arrhythmia detection and classification system 200 may additionally include an optional therapy circuit 260.

The sensor circuit 210 may receive physiologic information of a subject. In an example, the sensor circuit 210 include a sense amplifier circuit coupled to one or more physiologic sensors associated with the subject to sense a physiologic signal. The physiologic sensors may be implantable, wearable, or otherwise ambulatory sensors or electrodes attached to or implanted in a patient. Examples of the physiologic signals may include surface electrocardiography (ECG) such as sensed from electrodes on the body surface, subcutaneous ECG such as sensed from electrodes placed under the skin, intracardiac electrogram (EGM) sensed from the one or more electrodes on the lead system 108, heart rate signal, heart rate variability signal, pulsatile cardiac mechanical activity signal, thoracic or cardiac impedance signal, arterial pressure signal, pulmonary artery pressure signal, left atrial pressure signal, RV pressure signal, LV coronary pressure signal, coronary blood temperature signal, blood oxygen saturation signal, heart sound signal such as sensed by an ambulatory accelerometer or acoustic sensors, physiologic response to activity, apnea hypopnea index, one or more respiration signals such as a respiration rate signal or a tidal volume signal, among others. The sensor circuit 210 may include one or more other sub-circuits to digitize, filter, or perform other signal conditioning operations on the received physiologic signal. In some examples, physiologic information acquires from a patient may be stored in a storage device, such as an electronic medical record system, and the sensor circuit 210 may retrieve a physiologic signal from the storage device in response to a command signal that is provided by a system user, or automatically generated in response to occurrence of a specific event.

The correlator circuit 220 may generate autocorrelation sequences using the physiologic information received by the sensor circuit 210. In an example, the physiologic information includes cardiac activity information, such as ECG, intracardiac EGM, heart sounds, among other cardiac electrical or mechanical signals sensed from the patient. The correlator circuit 220 may generate from the cardiac signal a plurality of signal segments $\{X1, X2, \ldots, Xn\}$ beginning at respective elapsed time $\{t1, t2, \ldots, tn\}$ with respect to a reference time T0. That is, X1 begins at t1 seconds after T0, X2 beings at t2 seconds after T0, . . . , and Xn begins at tn seconds after T0. The signal segments have respective lengths or time durations $\{D1, D2, \ldots, Dn\}$. In an example, the durations are approximately 1-2 seconds. In an example, at least some of the signal segments have identical durations. Autocorrelation sequences $\{R1, R2, \ldots, Rn\}$ may be generated respectively for the signal segments $\{X1, X2, \ldots, Xn\}$. An autocorrelation sequence R(Xi) of the signal segment Xi represents a similarity of Xi and a delayed copy (with a time lag $\tau$) of the signal segment Xi itself. As such, the autocorrelation sequence R(Xi) may be expressed as a function of time lag $\tau$. Alternatively, in some examples, the time lag $\tau$ may be converted to number of samples (e.g., by multiplying $\tau$ by a signal sampling frequency), or heart rate in beats per minute (bpm) (e.g., by dividing 60 seconds by $\tau$ in seconds). Accordingly, R(Xi) may be expressed as a function of number of samples or heart rate. The autocorrelation sequence may be used to find repeating patterns (or signal periodicity), such as the presence of a periodic signal obscured by noise, or to identify the missing fundamental frequency in the corresponding signal segment. In an example, the autocorrelation sequence of a cardiac signal may be used to determine heart rate.

In some examples, the autocorrelation sequences $\{R1, R2, \ldots, Rn\}$ may be generated using a Minimum Absolute Difference (MAD) function, such as described separately in U.S. Pat. No. 9,451,893, titled "CALCULATION OF SELF-CORRELATION IN AN IMPLANTABLE CARDIAC DEVICE", and U.S. Pat. No. 9,629,565, titled "PEAK SELECTION FOR SELF CORRELATION ANALYSIS OF CARDIAC RATE IN AN IMPLANTABLE MEDICAL DEVICES." The MAD function includes a series of comparisons between (i) a comparator sequence, which is a portion of a signal, and (ii) the overall signal itself. The comparisons are performed by repeatedly shifting the comparator sequence relative to the overall signal. The MAD may be computed as the minimum of the absolute values of the differences between the comparator sequence and the overall signal. In some examples, the MAD function-based autocorrelation may be computed between first and second portions of a signal, where the second portion includes the first portion and is longer than the first portion. In an example, the second portion may be twice as long as the first portion. The first signal portion is then repeatedly subtracted from the second signal portion at a series of time lag $\tau$ (e.g., from zero lag to a lag of approximately the length of the first signal portion) to generate an autocorrelation sequence. By replacing multiplication operations in conventional autocorrelation computation (via a dot product) with subtraction, the MAD function reduces the number of required calculations by an order of magnitude or more, with minimal reduction in accuracy. U.S. Pat. Nos. 9,451,893, and 9,629,565 as mentioned above describe methods, techniques, and examples of generating autocorrelation sequence using MAD, finding autocorrelation peaks, estimating heart rates from the autocorrelation sequence, the disclosures of which are incorporated herein by reference.

Figure 4A:
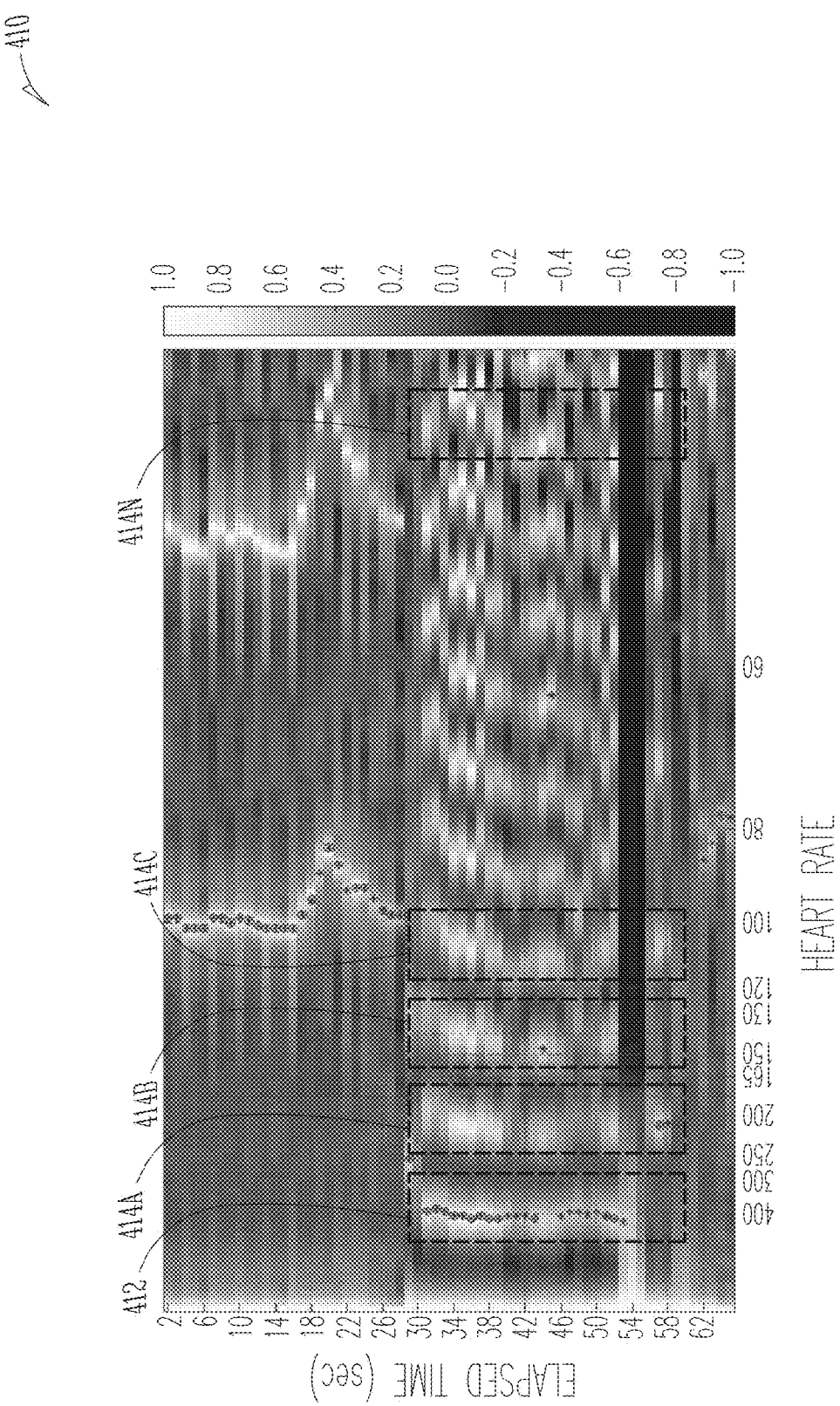
FIGS. 4A-4C are graphs illustrating examples of correlation images of various types of tachyarrhythmia and normal sinus rhythm.
Figure 4B:
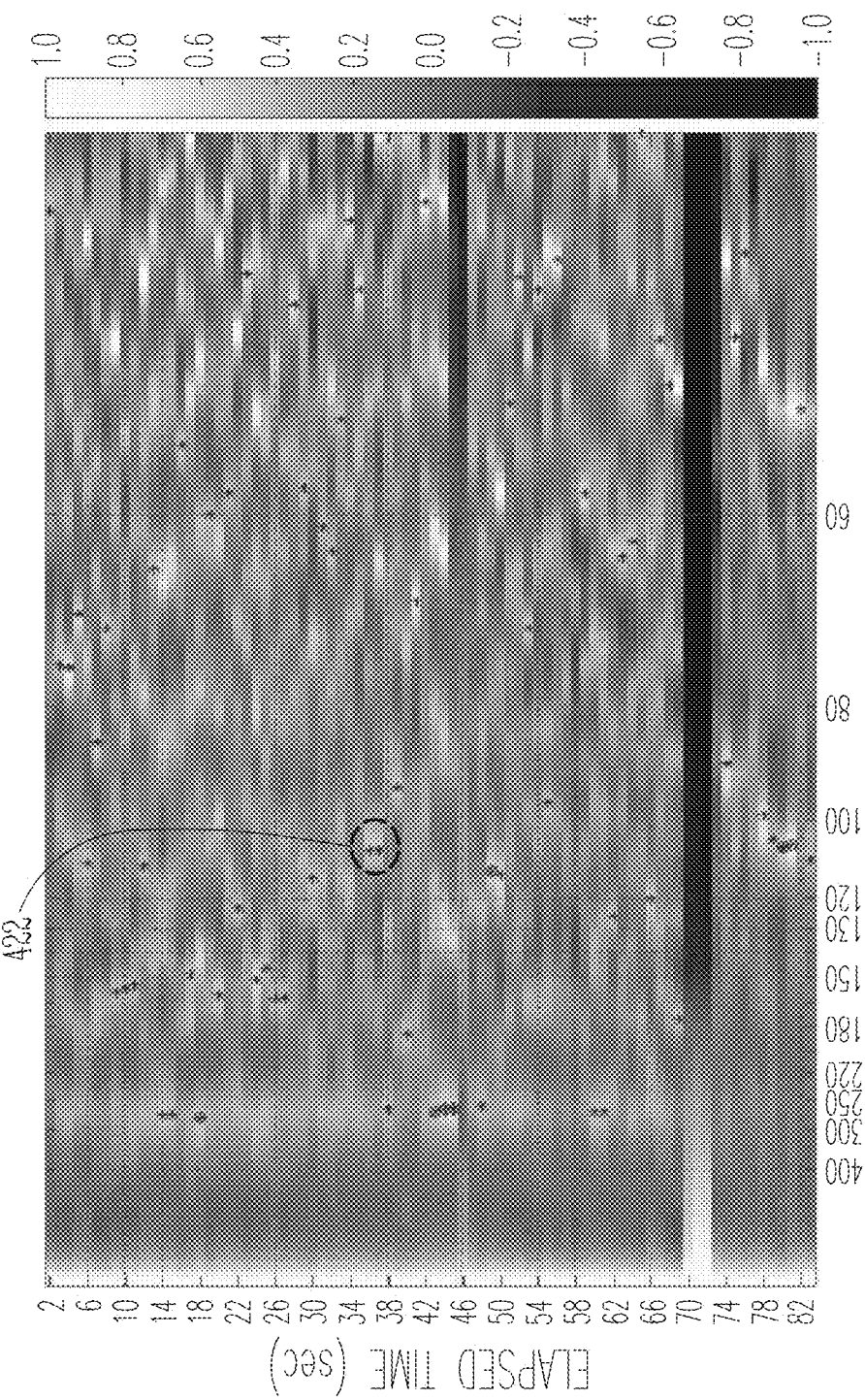
Figure 4C:
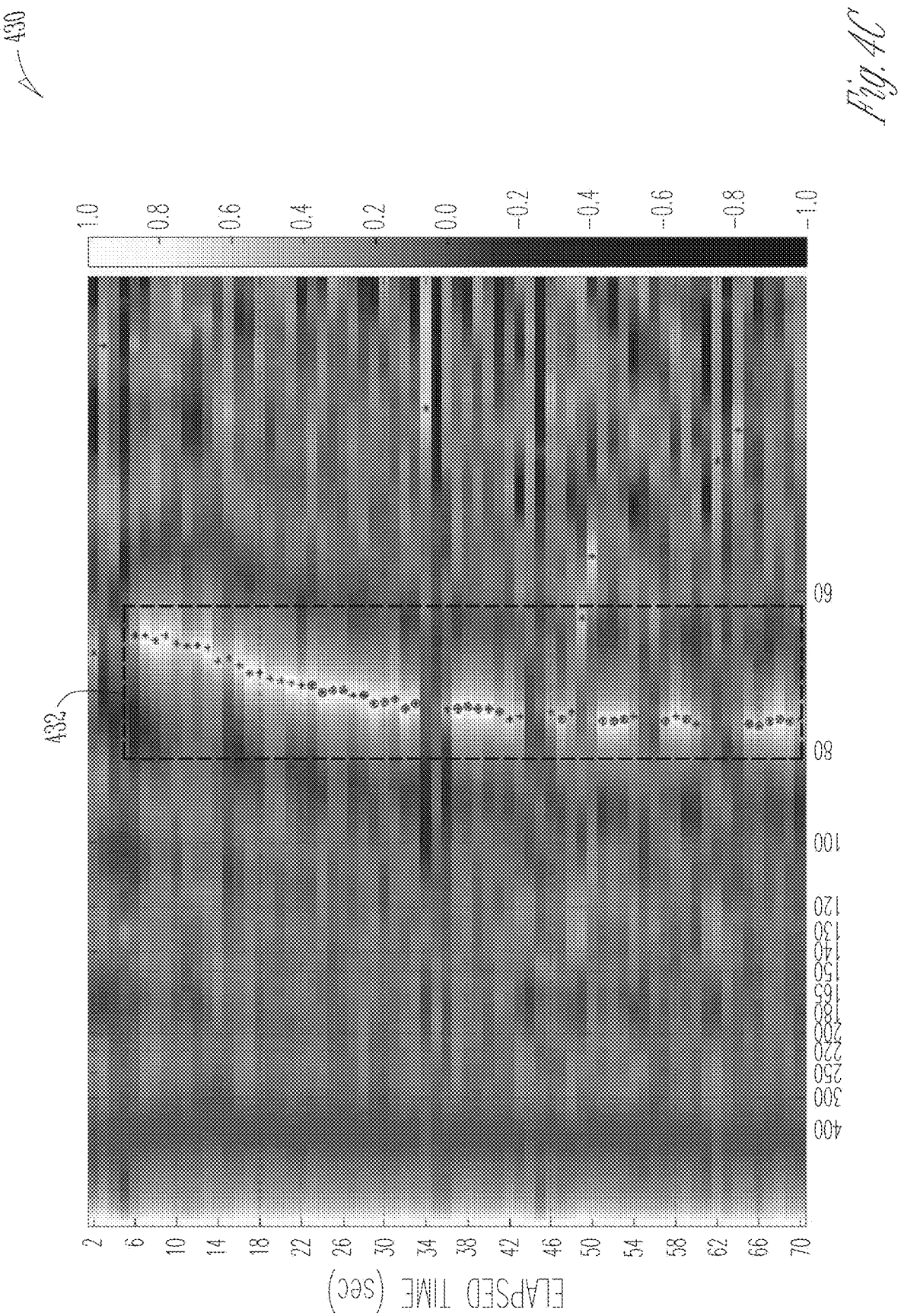

The correlation image generator 222 may be configured to construct a correlation image using the generated autocorrelation sequences. In an example, the autocorrelation sequences $\{R1, R2, \ldots, Rn\}$ may be stacked according to their corresponding elapsed time $\{t1, t2, tn\}$ to form a correlation image. The correlation image may be a three-dimensional (3D) representation of autocorrelation values over a range of heart rates (or the time lag τ values) and elapsed time {t1, t2, tn}. In some examples, the correlation image may be visually represented by a 3D gray-scale or color map, and presented on a display. By way of example, FIGS. 4A-4C illustrate 3D correlation images constructed using cardiac signals respectively acquired during tachyarrhythmia and normal sinus rhythm (NSR). In some examples, the correlation image may be represented by a 3D data array (or other data structures). The data array may be stored in the memory circuit 240, and used in applications such as arrhythmia detection and classification.

The arrhythmia detection/classification circuit 230 may be configured to detect tachyarrhythmia, and classify the cardiac activity as one of a plurality of arrhythmia types using the correlation image. To improve the quality of the correlation image, in some examples, the correlation image may be pre-processed to allow the arrhythmia detection/classification circuit 230 more easily identify key image features (e.g., value, timing, and temporal pattern of autocorrelation peaks) and improve classification performance. Examples of such image pre-processing may include resampling and/or digitization, filtering, image enhancement, image segmentation, etc. Image enhancement (e.g., image filtering or histogram equalization) may help remove or attenuate noise in the correlation image. Image segmentation may be based on thresholding the image intensity, edge detection, or clustering, etc. The arrhythmia detection/classification circuit 230 may feed the pre-processed correlation image, or a portion thereof, into an image recognition model. The image recognition model may include a rule-based model, or a template-based model. Examples of the image recognition model may include a linear regression model, a decision tree, a Naïve Bayes model, a support vector machine model, a K-nearest neighbor model, a random forest model, a neural network model, a voting model, a fuzzy logic model, among other machine-learning (ML) models. In some examples, the image recognition model may be a probabilistic model. Examples of the probabilistic model can include a Markov model, a hidden Markov model, a Bayesian network model, or a stochastic grammar model, among other stochastic graphical models.

The image recognition model may be trained via a model training process in a separate device, such as the external device 120 or the remote device 124. Training of the image recognition model may be carried out using a database of correlation images of a patient population. Once trained and satisfying a specified performance criterion, the image recognition model may be stored in the memory circuit 240, which may be accessible by the arrhythmia detection/classification circuit 230. Examples of training an image recognition model are discussed below, such as with reference to FIG. 3. The trained image recognition model has a specific model structure (e.g., nodes in a decision tree and the rules at the nodes, layers and neurons at each layer in an artificial neural network and integration rules at the neurons of the artificial neural network, etc.) and parameter values (e.g., weights or threshold values). The image recognition model has an output of one or more arrhythmia types, such as AF, AFL, AT, SVT, VT, or VF, etc. In some examples, the image recognition model may additionally output a confidence indication associated with the recognized arrhythmia type. The confidence indication may be determined using image features taken from the input correlation image or a portion thereof. The confidence indication may be represented by a numerical value, or a categorical value indicating discrete levels of arrhythmia classification confidence. In an example, the confidence indication may be determined based on a similarity between the correlation image and an image template.

In some examples, the arrhythmia detection/classification circuit 230 may feed into an image recognition model a set of sample image features extracted or otherwise measured from the correlation image (or a portion thereof). The sample image features may be predetermined, examples of which may include amplitudes, timing, slopes, widths, or signal power (e.g., area) of autocorrelation peaks in the correlation image. In some examples, the sample image features may include statistical image features, such as maximum, minimum, a central tendency, or variability of amplitudes of the autocorrelation peaks; or a scatteredness metric or other second- or higher-order statistics of locations of the autocorrelation peaks in the correlation image. Said statistical image features may be taken from autocorrelation measurements along the heart rates (or the time lag τ) dimension, the elapsed time dimension, or both. In some examples, the sample image features may additionally or alternatively include morphological features such as a collection of sample correlation values taken from one or more autocorrelation sequences, including characteristic points (e.g., the peaks, troughs, inflection points) and sample correlation values between the characteristic points.

In some examples, the image recognition model may be a template-based model. The arrhythmia detection/classification circuit 230 may classify an arrhythmia using template matching between (i) the patient correlation image (or a portion thereof) or image features extracted therefrom, and (ii) one or more image templates each representing a correlation image of a known arrhythmia type, such as an AF image template, VF image template, VT image template, etc. In an example, the image template may include a NSR image template. The arrhythmia detection/classification circuit 230 may classify the cardiac activity using a comparison of the correlation image to the one or more arrhythmia templates. In an example, a similarity metric may be computed between image features taken from the patient correlation image and image features taken from an arrhythmia template. The similarity metric may include a distance measure such as Euclidean distance, Mahalanobis distance, correlation coefficient, or a L1, L2, or infinite norm, among others. If the similarity metric exceeds a threshold, the patient correlation image is deemed similar to the image template, and the patient cardiac activity is classified as the arrhythmia type corresponding to the image template.

The memory circuit 240 may store the image recognition model, as discussed above. In some examples, the memory circuit 240 may store one or more arrhythmia templates each representing a correlation image of a known arrhythmia type (or NSR). The arrhythmia detection/classification circuit 230, coupled to the memory circuit 240, may receive the image recognition model to classify the arrhythmia. The memory circuit 240 may be communicatively coupled to an external system (e.g., external device 120 or the remote device 124) where an image recognition model may be trained, and replace the existing image recognition model stored in memory circuit 240 if necessary.

As illustrated in FIG. 2, the correlator circuit 220 and the arrhythmia detection/classification circuit 230 may respectively include circuit sets comprising one or more other circuits or sub-circuits. The circuits or sub-circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

In various examples, portions of the functions of the correlator circuit 220 and the arrhythmia detection/classification circuit 230 may be implemented as a part of a microprocessor circuit. The microprocessor circuit may be a dedicated processor such as a digital signal processor, application specific integrated circuit (ASIC), microprocessor, or other type of processor for processing information including the physiologic signals received from the sensor circuit 210. Alternatively, the microprocessor circuit may be a general-purpose processor that may receive and execute a set of instructions of performing the functions, methods, or techniques described herein.

The user interface unit 250 may include an input device and an output device. In an example, at least a portion of the user interface unit 250 may be implemented in the external system 130. The input device may receive a user's programming input, such as parameters for adjusting detection criterion and parameters for detecting cardiac arrhythmia. The input device may include a keyboard, on-screen keyboard, mouse, trackball, touchpad, touch-screen, or other pointing or navigating devices. The input device may enable a system user to program the parameters used for sensing the physiologic signals, detecting the arrhythmias, and generating alerts, among others.

The output device may generate a human-perceptible presentation of the detected cardiac arrhythmia. The output device may include a display for displaying the sensed physiologic signal, intermediate measurements or computations such as correlation sequences, correlation image, or template image of a known arrhythmia type, among others. The output unit may include a printer for printing hard copies of the detection information. The information may be presented in a table, a chart, a diagram, or any other types of textual, tabular, or graphical presentation formats. The presentation of the output information may include audio or other media format to alert the system user of the detected arrhythmic events. In an example, the output device may generate alerts, alarms, emergency calls, or other forms of warnings to signal the system user about the detected arrhythmic events.

The optional therapy circuit 260 may be configured to deliver a therapy to the patient in response to the detected cardiac arrhythmia. Examples of the therapy may include electrostimulation therapy delivered to the heart, a nerve tissue, other target tissues, a cardioversion therapy, a defibrillation therapy, or drug therapy. In some examples, the therapy circuit 260 may modify an existing therapy, such as adjust a stimulation parameter or drug dosage.

Figure 3:
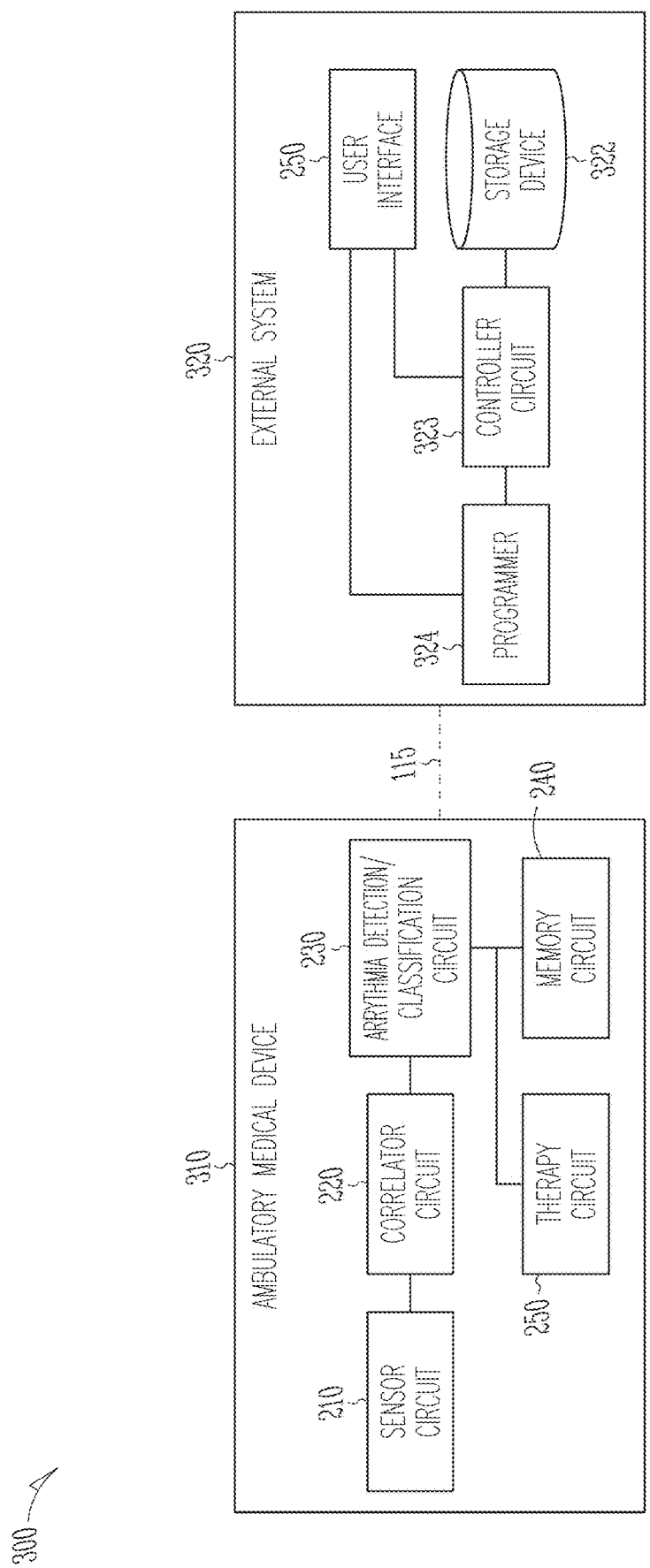
FIG. 3 illustrates a block diagram of another example of an arrhythmia detection and classification system.

FIG. 3 illustrates a block diagram of another example of an arrhythmia detection and classification system 300, which is an embodiment of the arrhythmia detection and classification system 200. The arrhythmia detection and classification system 300 may include an ambulatory medical device (AMD) 310 and an external system 320 communicatively coupled to the AMD 310 via the communication link 115. The AMD 310 is an embodiment of the AMD 110, and may include several components of the system 200, including the sensor circuit 210, the correlator circuit 220, the arrhythmia detection/classification circuit 230, the memory circuit 240, and the therapy circuit 260. The external system 320 is an embodiment of the external system 125, and may include the user interface 250, a storage device 322, a controller circuit 323, and a programmer circuit 324. The storage device 322 may store a database of correlation images of a patient population. The correlation images in the database may be generated by multiple devices (including the AMD 310) communicatively coupled to the external system 125. The controller circuit 323 may generate an image recognition model, such as through a model training process using the image database in the storage device 322. The model training may include an optimization process (e.g., gradient descent), in which a model parameter (e.g., a structural element such as a node in a layer of a neural network, or a weight factor associated with the node) is adjusted until a desirable performance is achieved (e.g., minimizing a loss function). The trained image recognition model has an optimized model structure and optimized model parameter values. In some examples, the controller circuit 323 may update the image recognition model periodically, or triggered by a user command (e.g., via the user interface 250) or a specified event, such as a change in patient medical condition or when new correlation images become available in the storage device 322.

The programmer circuit 324 may produce parameter values for operating the AMD 310, including parameters for sensing the signals and generating signal metrics, and parameters or electrode configurations for delivering therapy (e.g., cardiac pacing, or defibrillation). The programmer circuit 324, which may be coupled to the controller circuit 323, may initiate transmission of the trained image recognition model to the AMD 310 and store it in the memory circuit 240. In an example, to save communication bandwidth and reduce transmission latency, the external system 320 may compare the newly trained image recognition model to a copy of the pre-existing model in the memory circuit 240, and determine any differences between the two models. The programmer 324 may transmit said differences to the memory circuit 240 via the communication link 115. The pre-exiting model in the memory circuit 240 may then be updated with said differences.

In some examples, the programmer circuit 324 may provide stimulation parameters or electrode configuration to the AMD 310. The programmer circuit 324 may be coupled to the user interface 250 to allow a user to confirm, reject, or edit the stimulation parameters, sensing parameters, or other parameters controlling the operation of the AMD 310. The programmer circuit 324 may also adjust the stimulation parameter or electrode configuration in a commanded mode upon receiving from a system user a command or confirmation of parameter adjustment.

FIGS. 4A-4C illustrate examples of correlation images corresponding to arrhythmias or NSR, according to some embodiments discussed in this document. The correlation images may each be constructed by the correlation image generator 222, by stacking multiple autocorrelation sequences generated using respective segments of a cardiac signal (e.g., an ECG, an intracardiac EGM, or a cardiac mechanical activity signal) acquired when a patient experiences a particular type of cardiac arrhythmia or NSR. The signal segments have a predetermined length of approximately 1-2 seconds. The signal segments can be consecutive in time, or overlap between adjacent segments. The correlation sequences in these examples were computed using a modified correlation technique based on a Minimum Absolute Difference (MAD) function, as described in U.S. Pat. Nos. 9,451,893 and 9,629,565, the disclosures of which are incorporated herein by reference. The correlation images are displayed as a 3D grayscale or color image representing correlation values over heart rates (derived from the time lag $\tau$) and elapsed time with respect to a reference time. The heart rate is shown in the horizontal axis, and increases in a direction as indicated by the arrow. The elapsed time is shown in the vertical axis, and increases in a direction as indicated by the arrow. A row of the correlation image, corresponding to a particular elapsed time and extends throughout the displayed range of heart rates, represents a correlation sequence generated from the signal segment at that particular elapsed time.

FIG. 4A illustrates an exemplary VF correlation image 410. In this example, dominant autocorrelation peaks 412 occur at a heart rate of approximately 400 bpm, and sustain during a range of elapsed time approximately 30-55 seconds after a reference time. In this document, a dominant autocorrelation peak in a correlation sequence refers to a peak with a higher amplitude than other (non-dominant) autocorrelation peaks throughout the displayed range of time lag $\tau$ (or heart rate), excluding the peak at zero lag (i.e., $\tau=0$). In some examples, the dominant autocorrelation peak corresponds to the shortest time lag $\tau$ (or equivalently, the highest heart rate) in a correlation sequence. In FIG. 4A, for the correlation sequences falling within the elapsed time of approximately 30-55 seconds, the dominant autocorrelation peaks 412 consistently occur at approximately 400 bpm. Additionally, the VF correlation image 410 also shows a "picket fence" pattern, represented by dominant autocorrelation peaks 412 followed by non-dominant autocorrelation peaks 414A, 414B, 414C, . . . , 414N, that occur at substantially the same elapsed time range (approximately 30-55 seconds), but correspond to lower heart rates (or longer time lag $\tau$) than the dominant autocorrelation peaks 412. In this document, the pickets refer to autocorrelation peaks in a correlation sequence that occur at multiples of the time lag $\tau$ at which the dominant autocorrelation peaks occur (or equivalently, at fractions of the heart rate corresponding to the dominant autocorrelation peaks). The non-dominant autocorrelation peaks 414A-414N at lower heart rates represent various harmonics of the dominant autocorrelation peaks 412. A user may define a range of time lag $\tau$, such as $\tau_{min}<\tau<\tau_{max}$, for computing the correlation sequences and thus the correlation image. The defined range of time lag $\tau$ corresponds to a displayed range of heart rates in the correlation image $HR_{min}<HR<HR_{max}$. For example, $HR_{min}$ corresponds to $\tau_{max}$. Due to the limited range of HR, generally the non-dominant autocorrelation peaks (e.g., 414A-414N) and the picket fence pattern can only be observed when the dominant autocorrelation peaks (e.g., peaks 412) occur at high heart rates (characteristic of VT or VF). If the dominant autocorrelation peaks occur at relatively lower heart rates (e.g., a NSR), the non-dominant peaks and the picket fence pattern would not be displayed in the correlation image (for example, see FIG. 4C). The arrhythmia detector/classification circuit 230 may apply the image recognition model stored in the memory circuit 240 to the correlation image 410, and recognize the underlying cardiac activity as VF based on the image features such as timing (e.g., heart rates) and/or pattern (e.g., picket fence pattern) of the autocorrelation peaks. In some examples, the arrhythmia detector/classification circuit 230 may classify the cardiac activity as VF if a similarity metric between the correlation image 410 and a VF image template exceeds a threshold.

FIG. 4B illustrates an exemplary AF correlation image 420. Using an image recognition model, the arrhythmia detector/classification circuit 230 may detect autocorrelation peaks (marked by asterisks in FIG. 4B, such as 422) from the correlation image, and generate image features such as timings of the autocorrelation peaks and a variability metric of said timings. The timing and timing variability of the autocorrelation peaks may be measured along the heart rate dimension, the elapsed time dimension, or in the joint heart rate-elapsed time dimensions (hereinafter referred to as "spatial" variability). In an example, a spatial distribution (e.g., a histogram) of the autocorrelation peak timings in the joint heart rate-elapsed time dimensions may be generated, and the features may be extracted from said spatial distribution. The arrhythmia detector/classification circuit 230 may recognize the underlying cardiac activity as AF based on image features such as timings, timing variability, or spatial distribution features of the autocorrelation peaks. In some examples, the arrhythmia detector/classification circuit 230 may alternatively classify the cardiac activity as AF if a similarity metric between the correlation image 420 and an AF image template exceeds a threshold.

FIG. 4C illustrates an exemplary NSR correlation image 430 for the purpose of comparison with the correlation images of arrhythmias, such as the VF correlation image 410 and the AF correlation image 420. The correlation image 430 shows dominant autocorrelation peaks 432 occurred at a heart rate of approximately 70-80 bpm. The autocorrelation peak amplitude is relatively consistent over a wide range of elapsed time. Compared to VF correlation image 410, no "picket fence" pattern is observed in the NSR correlation image. This is because at a lower heart rate below a preset threshold (e.g., 60, 75, or 90 bpm), the time span of the time lag $\tau$ (and thus the heart rate in the horizontal axis) for computing the correlation sequence may not be sufficient to produce a picket pattern for all heart rates, particularly for lower heart rates with longer beat intervals, a characteristic of NSR. Using an image recognition model, the arrhythmia detector/classification circuit 230 may recognize the underlying cardiac activity as NSR based on image features such as the heart rate and heart rate variability of the autocorrelation peaks, consistency of the autocorrelation peak amplitude, or a pattern of the autocorrelation peaks in the joint heart rate-elapsed time dimensions (e.g., an absence of the "picket fence" pattern.) Alternatively, the arrhythmia detector/classification circuit 230 may classify the cardiac activity as NSR if a similarity metric between the correlation image 420 and an NSR image template exceeds a threshold.

Figure 5:
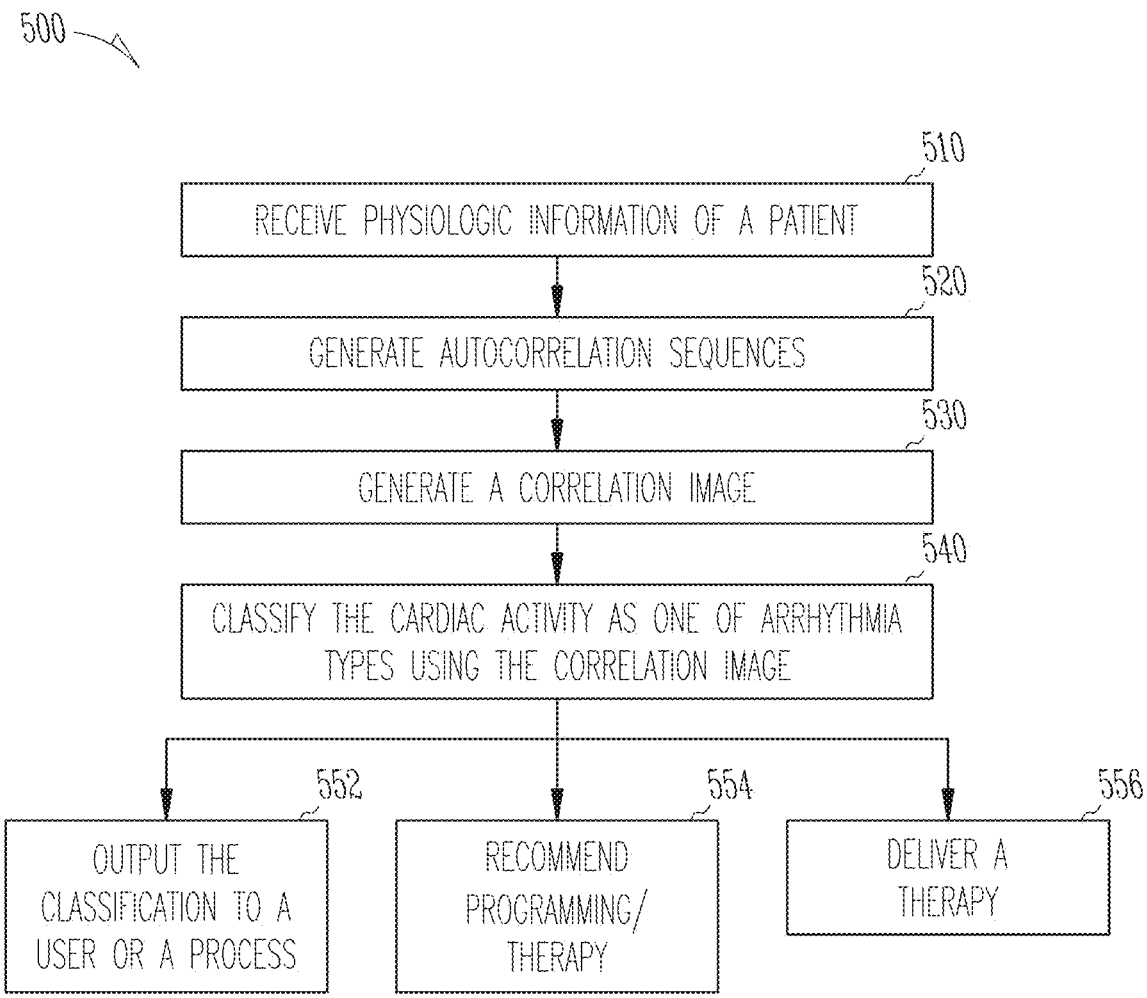
FIG. 5 is a flowchart illustrating an example of a method for detecting and classifying cardiac arrhythmia in a subject.

FIG. 5 is a flowchart illustrating an example of a method 500 for detecting and classifying cardiac arrhythmia in a subject. Examples of cardiac arrhythmia may include AF, AFL, AT, SVT, VT, VF, or cardiac pauses, among other brady- or tachy-arrhythmia. The method 500 can be implemented in and executed by an ambulatory medical device, such as an implantable or wearable device, or in a remote patient management system. In an example, the method 500 may be implemented in the physiologic event detector circuit 160 of the AMD 110, the external system 125, or the arrhythmia detection and classification system 200.

The method 500 commences at step 510, where physiologic information of a patient may be received. The physiologic information may include physiologic signals sensed by one or more implantable, wearable, or otherwise ambulatory sensors. Examples of the physiologic signals may include cardiac electrical signals, such as ECG or EGM, or signals indicative of cardiac mechanical activity, such as pressure, impedance, heart sounds, or respiration signals. The sensed physiologic signal may be pre-processed, including amplification, digitization, filtering, or other signal conditioning operations. In some examples, patient physiologic signals may be sensed and stored in a storage device, such as an electronic medical record system, and retrieved for use such as according to the method 500.

At 520, autocorrelation sequences may be generated using the physiologic information, such as using the correlator circuit 220. In an example, a plurality of signal segments may be taken from a cardiac signal (e.g., ECG, intracardiac EGM, or a cardiac mechanical signal such as a heart sounds signal). The signal segments correspond to respective elapsed time with respect to a reference time. Autocorrelation sequences may be generated respectively for the signal segments. An autocorrelation sequence may be expressed as a function of time lag $\tau$. In some examples, the time lag $\tau$ may be converted to heart rate in beats per minute (bpm), and the autocorrelation sequence may be expressed as a function of heart rate. In some examples, autocorrelation sequences may be generated using a modified and more efficient method based on a Minimum Absolute Difference (MAD) function. The MAD function includes a series of comparisons between (i) a comparator sequence, which is a portion of a signal, and (ii) the overall signal itself. The comparisons are performed by repeatedly shifting the comparator sequence relative to the overall signal. Differences between the comparator sequence and the overall signal may be computed, and MAD may be computed as the minimum of the absolute values of the differences. Compared to, the MAD-based correlation replaces multiplications (involved in conventional correlation) with subtraction, thereby substantially reducing the number of required calculations. U.S. Pat. No. 9,451,893, titled "CALCULATION OF SELF-CORRELATION IN AN IMPLANTABLE CARDIAC DEVICE", and U.S. Pat. No. 9,629,565, titled "PEAK SELECTION FOR SELF CORRELATION ANALYSIS OF CARDIAC RATE IN AN IMPLANTABLE MEDICAL DEVICES" describe methods, techniques, and examples of generating autocorrelation sequence using MAD, and finding signal metrics such as autocorrelation peaks or heart rates estimates from the autocorrelation sequence, the disclosures of which are incorporated herein by reference.

At 530, a correlation image may be constructed using the generated autocorrelation sequences, such as by the correlation image generator 222. The correlation image may be generated by stacking the autocorrelation sequences according to their corresponding elapsed time with respect to a reference time. In some examples, the correlation image may be represented by a three-dimensional (3D) array consisting of correlation values at corresponding heart rates (or the time lag $\tau$) and elapsed time. The correlation image may be visually represented by a 3D image, such as a grayscale or color map that represents correlation values over a range of heart rates (e.g., derived from the time lag $\tau$) and elapsed time with respect to a reference time, examples of which are shown in FIGS. 4A-4C as discussed above.

At 540, the underlying cardiac activity may be classified as one of a plurality of arrhythmia types using the correlation image, such as by using the arrhythmia detection/classification circuit 230. A correlation image, or a portion thereof, may be fed into an image recognition model, which may select image features and recognize arrhythmia using trained rules implemented in the model. In some example, to improve correlation image quality and facilitate image feature extraction, the correlation image may be pre-processed (e.g., through image enhancement and image segmentation). In some examples, a set of sample image features may be extracted or otherwise measured from the correlation image (or a portion thereof), and fed into the image recognition model. The sample image features may include peak autocorrelation values take from one or more autocorrelation sequences, or timing, positive or negative slopes, or signal power of said autocorrelation peaks. The sample image features may include statistical measurements of the peak autocorrelations, such as maximum, minimum, or a central tendency of the autocorrelation peaks, a scatteredness metric indicative of variability of the autocorrelation peaks, or other second- or higher-order statistics of the autocorrelation peaks or characteristics taken from the correlation image. Said statistical measurements may be performed on measurement along the heart rates (or the time lag $\tau$) dimension, the elapsed time dimension, or both. In some examples, the sample image features may include morphological features such as a collection of sample correlation values taken from one or more autocorrelation sequences, including characteristic points (e.g., the peaks, troughs, inflection points) and sample correlation values between said characteristic points. In some examples, one or more dominant autocorrelation peaks and one or more non-dominant peaks may be detected from the correlation image. An image feature representing a spatial pattern of the one or more dominant autocorrelation peaks and the one or more non-dominant peaks may be used to classify an arrhythmia, such as a "picket fence" pattern represented by dominant autocorrelation peaks followed by non-dominant autocorrelation peaks, an example of which is illustrated in FIG. 4A.

The image recognition model may be trained via a model training process in a separate device, such as the external device 120, the remote device 124, or the external system 320 as discussed above with reference to FIG. 3. The image recognition model may be a rule-based model, or a template-based model. Examples of the image recognition model may include a linear regression model, a decision tree, a Naïve Bayes model, a support vector machine model, a K-nearest neighbor model, a random forest model, a neural network model, a voting model, a fuzzy logic model, among other machine-learning (ML) models. In some examples, the image recognition model may be a probabilistic model. Examples of the probabilistic model can include a Markov model, a hidden Markov model, a Bayesian network model, or a stochastic grammar model, among other stochastic graphical models. In some examples, the image recognition model may be a template-based model. The arrhythmia classification may include a template matching between (i) the correlation image (or a portion thereof) of the subject or image features extracted therefrom, and (ii) one or more image templates each representing a correlation image of a known arrhythmia type (and optionally a NSR), such as an AF image template, VF image template, VT image template, NSR image template, etc. A similarity metric may be computed between the image features taken from the correlation image and the image features taken from an arrhythmia template. The similarity metric may be compared to a threshold or a threshold range to determine whether the correlation image is similar to the image template, and if so, classify the cardiac activity as the arrhythmia type corresponding to said image template.

The arrhythmia classification of the cardiac activity may be provided to one or more processes 552, 554, or 556. At 552, the arrhythmia classification may be output to a user or a process, such as via an output device of the user interface 250. In an example, physiologic information (e.g., a physiologic sensor signal), one or more correlation sequences, or the correlation image (e.g., one of FIGS. 5A-5C) may be displayed on a display unit. Hard copies of the detection information may be generated. In various examples, alerts, alarms, emergency calls, or other forms of warnings may be generated to signal the system user about the detected and classified arrhythmia.

At 554, a recommendation may be generated and provided to a user. The recommendation may include one or more of further diagnostic tests (e.g., arrhythmia classification) to be performed, or anti-arrhythmic therapy to be delivered. The recommendation may include adjustment of one or more arrhythmia classification parameters, such as the image recognition model configuration or model parameter values. The method 500 may include the optional step 556 of delivering a therapy to the patient in response to the arrhythmia classification, such as via the optional therapy circuit 260 as illustrated in FIG. 2. Examples of the therapy may include electrostimulation therapy delivered to the heart, a nerve tissue, other target tissues, a cardioversion therapy, a defibrillation therapy, or drug therapy including delivering drug to a tissue or organ. In some examples, an existing therapy or treatment plan may be modified to treat the detected arrhythmia.

Figure 6:
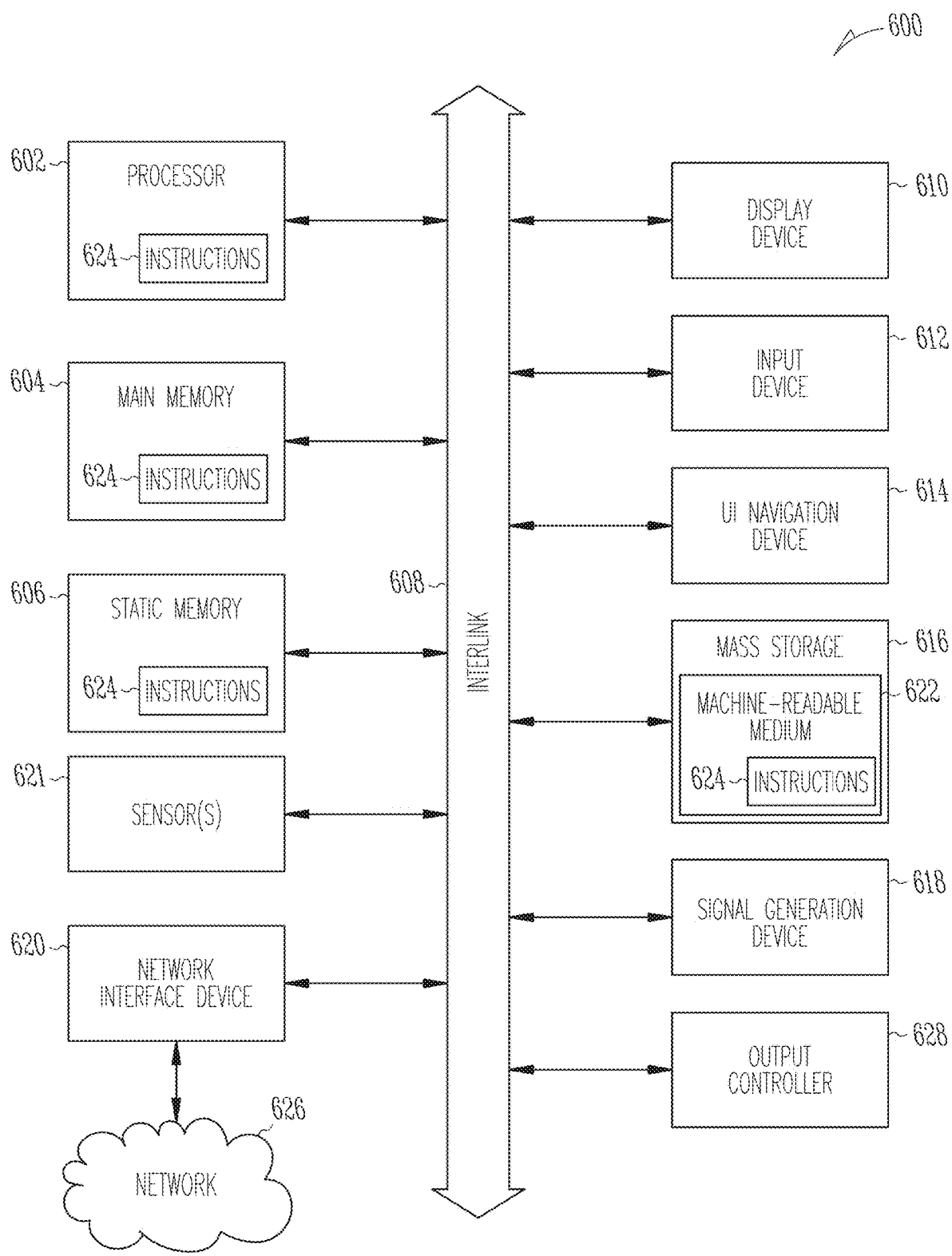
FIG. 6 illustrates generally a block diagram of an example machine upon which any one or more of the techniques (e.g., methodologies) discussed herein may perform.

FIG. 6 illustrates generally a block diagram of an example machine 600 upon which any one or more of the techniques (e.g., methodologies) discussed herein may perform. Portions of this description may apply to the computing framework of various portions of the IMD 110 or the external system 125, etc.

In alternative embodiments, the machine 600 may operate as a standalone device or may be connected (e.g., networked) to other machines. In a networked deployment, the machine 600 may operate in the capacity of a server machine, a client machine, or both in server-client network environments. In an example, the machine 600 may act as a peer machine in peer-to-peer (P2P) (or other distributed) network environment. The machine 600 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 600 may include a hardware processor 602 (e.g., a central processing unit (CPU), a graphics processing unit (GPU), a hardware processor core, or any combination thereof), a main memory 604 and a static memory 606, some or all of which may communicate with each other via an interlink (e.g., bus) 608. The machine 600 may further include a display unit 610 (e.g., a raster display, vector display, holographic display, etc.), an alphanumeric input device 612 (e.g., a keyboard), and a user interface (UI) navigation device 614 (e.g., a mouse). In an example, the display unit 610, input device 612 and UI navigation device 614 may be a touch screen display. The machine 600 may additionally include a storage device (e.g., drive unit) 616, a signal generation device 618 (e.g., a speaker), a network interface device 620, and one or more sensors 621, such as a global positioning system (GPS) sensor, compass, accelerometer, or other sensors. The machine 600 may include an output controller 628, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 616 may include a machine readable medium 622 on which is stored one or more sets of data structures or instructions 624 (e.g., software) embodying or utilized by any one or more of the techniques or functions described herein. The instructions 624 may also reside, completely or at least partially, within the main memory 604, within static memory 606, or within the hardware processor 602 during execution thereof by the machine 600. In an example, one or any combination of the hardware processor 602, the main memory 604, the static memory 606, or the storage device 616 may constitute machine-readable media.

While the machine-readable medium 622 is illustrated as a single medium, the term "machine readable medium" may include a single medium or multiple media (e.g., a centralized or distributed database, and/or associated caches and servers) configured to store the one or more instructions 624.

The term "machine readable medium" may include any medium that is capable of storing, encoding, or carrying instructions for execution by the machine 600 and that cause the machine 600 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 624 may further be transmitted or received over a communications network 626 using a transmission medium via the network interface device 620 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 620 may include one or more physical jacks (e.g., Ethernet, coaxial, or phone jacks) or one or more antennas to connect to the communications network 626. In an example, the network interface device 620 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 600, and includes digital or analog communications signals or other intangible medium to facilitate communication of such software.

Various embodiments are illustrated in the figures above. One or more features from one or more of these embodiments may be combined to form other embodiments.

The method examples described herein may be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code may be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system, comprising:
    a sensor circuit configured to sense cardiac activity including a cardiac signal from a subject;
    a correlator circuit configured to:
        generate signal segments from the cardiac signal, each of the signal segments starting at a respective elapsed time after a common reference time;
        for each of the signal segments, generate an autocorrelation sequence representing autocorrelation values over a plurality of time lags; and
        generate correlation image data by arranging a plurality of the generated autocorrelation sequences along a dimension of the respective elapsed times of the signal segments;
    an arrhythmia classifier circuit configured to process the generated correlation image data to automatically extract an image feature, and to classify the cardiac activity of the subject as a particular arrhythmia using the automatically extracted image feature; and
    a user interface configured to display the classified arrhythmia to a user.

2. The system of claim 1, wherein the particular arrhythmia includes an atrial tachyarrhythmia or a ventricular tachyarrhythmia.

3. The system of claim 1, wherein the correlator circuit is configured to determine a range of heart rates using the plurality of time lags, and to generate the correlation image data including a three-dimensional representation of the autocorrelation values over the range of heart rates and a range of the elapsed times of the signal segments.

4. The system of claim 1, wherein the generation of an autocorrelation sequence, for a first signal segment from the generated signal segments, includes:
    selecting a second signal segment from the generated signal segments, the second signal segment including the first signal segment and longer than the first signal segment; and
    generating the autocorrelation sequence, corresponding to the first signal segment, using repeated subtractions of the first signal segment from the second signal segment at the plurality of time lags.

5. The system of claim 1, wherein the arrhythmia classifier circuit is configured to detect one or more autocorrelation peaks from the correlation image, and to extract the image feature including one or more of an amplitude, a timing, or a scatteredness metric of the detected one or more autocorrelation peaks.

6. The system of claim 5, wherein the arrhythmia classifier circuit is configured to detect from the correlation image one or more dominant autocorrelation peaks and one or more non-dominant peaks, and to extract the image feature including a temporal pattern of the one or more dominant autocorrelation peaks and the one or more non-dominant peaks.

7. The system of claim 1, wherein the arrhythmia classifier circuit further comprises an image recognition model, the arrhythmia classifier circuit configured to classify the cardiac activity further using the image recognition model.

8. The system of claim 7, wherein the image recognition model includes an arrhythmia template representing correlation image data of a known arrhythmia, and wherein the arrhythmia classifier circuit is configured to compare the generated correlation image data to the arrhythmia template, and to classify the cardiac activity using the comparison.

9. The system of claim 7, further comprising: a database of correlation images; and a controller circuit configured to generate or update the image recognition model using the database of correlation images.

10. The system of claim 9, further comprising an ambulatory device configured to be implanted in or worn by the subject and a remote computing device configured to communicate with the ambulatory device, the ambulatory device including the arrhythmia classifier circuit, and the remote computing device including the controller circuit.

11. The system of claim 1, further comprising a therapy circuit configured to deliver or adjust delivery of a therapy for the subject in response to the classified arrhythmia.

12. The system of claim 1, wherein the correlation image data includes a three-dimensional data array of correlation values over the respective elapsed times and the plurality of time lags.

13. The system of claim 1, wherein the correlation circuit is configured to generate a graphical representation of the correlation image on the user interface.

14. The system of claim 1, wherein the arrhythmia classifier circuit is configured to automatically extract one or more of a morphological feature or a statistical feature from the correlation image.

15. A method of classifying a cardiac arrhythmia, comprising:
  sensing cardiac activity including a cardiac signal of a subject using a sensor circuit;
  generating, via a correlator circuit, signal segments from the cardiac signal, each of the signal segments starting at a respective elapsed time after a common reference time;
  for each of the signal segments, generate an autocorrelation sequence representing autocorrelation values over a plurality of time lags using the correlator circuit;
  generating, via the correlator circuit, correlation image data by arranging a plurality of the generated autocorrelation sequences along a dimension of the respective elapsed times of the signal segments;
  automatically extracting, via an arrhythmia classifier circuit, an image feature from the correlation image data;
  classifying, via the arrhythmia classifier circuit, the cardiac activity of the subject as a particular arrhythmia using the automatically extracted image feature; and
  displaying on a user interface the classified arrhythmia.

16. The method of claim 15, comprising determining a range of heart rates using the plurality of time lags, and generating the correlation image data including a three-dimensional representation of the autocorrelation values over the range of heart rates and a range of the elapsed times of the signal segments.

17. The method of claim 15, wherein generating an autocorrelation sequence, for a first signal segment from the generated signal segments, includes:
  selecting a second signal segment from the generated signal segments, the second signal segment including the first signal segment and longer than the first signal segment; and
  generating the autocorrelation sequence, corresponding to the first signal segment, using repeated subtractions of the first signal segment from the second signal segment at the plurality of time lags.

18. The method of claim 15, comprising extracting an image feature from the correlation image, and classifying the cardiac activity of the subject as the particular arrhythmia using the extracted image feature,
  wherein the extracted image feature includes one or more of an amplitude, a timing, a scatteredness metric, or a temporal pattern of one or more autocorrelation peaks.

19. The method of claim 15, wherein classifying the cardiac activity includes using an image recognition model.

20. The method of claim 19, further comprising training the image recognition model using a database of correlation images.

* * * * *